United States Patent [19]

Evans et al.

[11] Patent Number: 5,542,928

[45] Date of Patent: Aug. 6, 1996

[54] METHOD AND DEVICE FOR THERMAL ABLATION HAVING IMPROVED HEAT TRANSFER

[75] Inventors: Michael A. Evans, Palo Alto; Colin J. Nichols, Fremont; Laura Kemp, Saratoga; William R. Dubrul, Redwood city; Robert S. Behl, Palo Alto, all of Calif.

[73] Assignee: InnerDyne, Inc., Sunnyvale, Calif.

[21] Appl. No.: 266,037

[22] Filed: Jun. 27, 1994

Related U.S. Application Data

[63] Continuation-in-part of Ser. No. 073,639, Jun. 7, 1993, Pat. No. 5,433,708, which is a continuation of Ser. No. 702,796, May 17, 1991, abandoned.

[51] Int. Cl.⁶ .................. A61F 7/00; A61B 17/36
[52] U.S. Cl. .................. 604/113; 606/27; 606/30
[58] Field of Search ............... 606/27–31; 604/113, 604/114; 607/96, 138, 104–107

[56] References Cited

U.S. PATENT DOCUMENTS

| | | | |
|---|---|---|---|
| 4,160,455 | 7/1979 | Law | 604/113 X |
| 4,676,258 | 6/1987 | Inokochi et al. | 606/27 X |
| 4,709,698 | 12/1987 | Johnston et al. | 604/114 X |
| 4,955,377 | 9/1990 | Lennox et al. | 606/27 X |
| 5,045,056 | 9/1991 | Behl | 604/113 X |
| 5,084,044 | 1/1992 | Quint | 606/27 |
| 5,100,388 | 3/1992 | Behl et al. | 604/113 |

*Primary Examiner*—Gary Jackson
*Assistant Examiner*—Nancy Mulcare
*Attorney, Agent, or Firm*—Townsend and Townsend and Crew LLP

[57] ABSTRACT

A thermal ablation catheter includes an elongate body member having a heating element disposed over a predetermined length of its distal end or within an axial lumen. The heating element is suspended away from an exterior surface of the elongate member to form a circulation region thereunder. Alternatively, the heating element is distributed over some or all of the axial lumen. Thermally conductive fluid can be introduced through the lumen in the elongate member and into the circulation region to effect heat transfer. The catheter is used to introduce the thermally conductive medium to a hollow body organ where the heating element raises the temperature of the medium sufficiently to induce injury to the lining of the organ. Optionally, an expandable cage in the catheter or on an associated introducer sheath may be used in combination with a thermal ablation catheter. The expandable cage helps center the heating element on the catheter within the body organ and prevents direct contact between the heating element and the wall of the organ. When disposed on the catheter, the cage can be useful to position a flow directing element attached to the flow delivery lumen of the catheter. Heat transfer and temperature uniformity can be enhanced by inducing an oscillatory flow of the heat transfer medium through the catheter while heat is being applied.

79 Claims, 10 Drawing Sheets

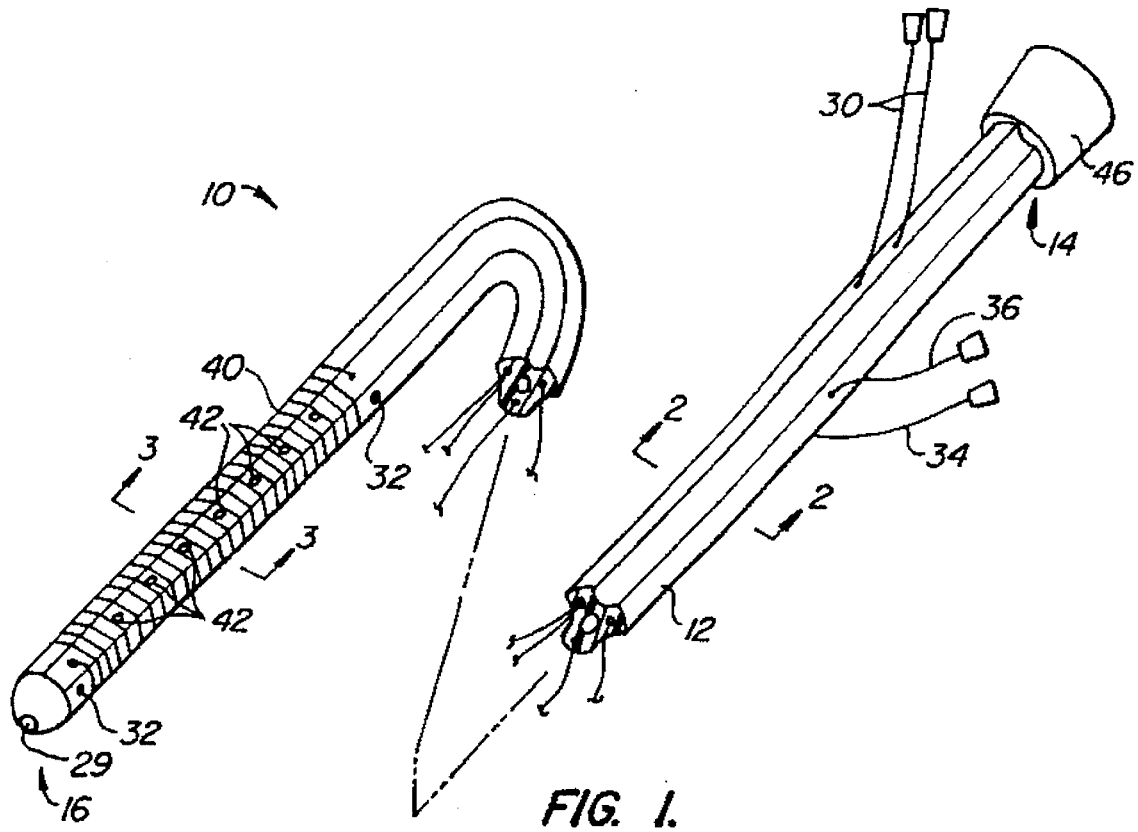
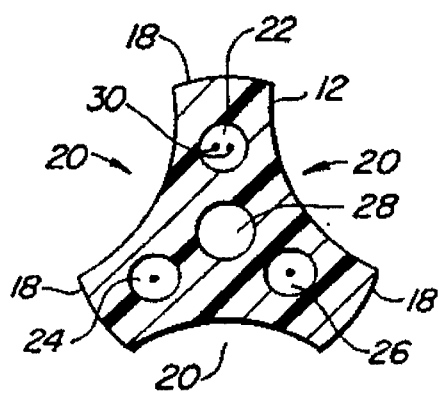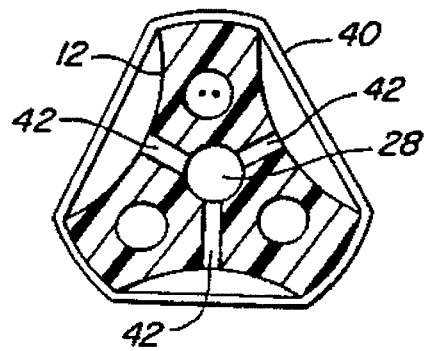
FIG. 1.
FIG. 2.
FIG. 3.

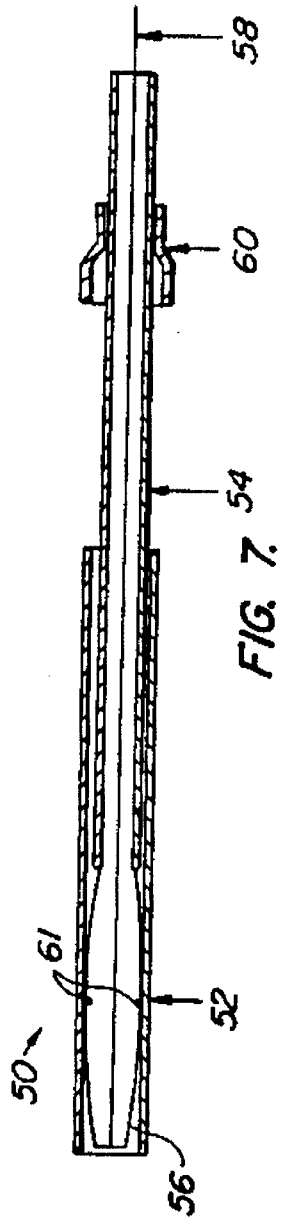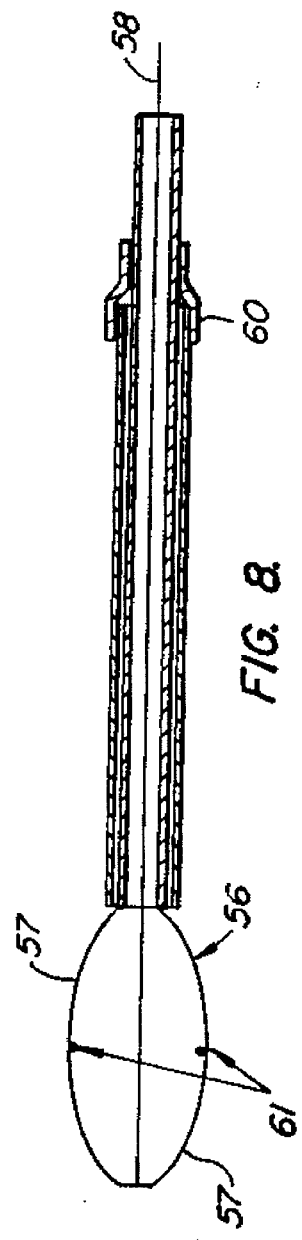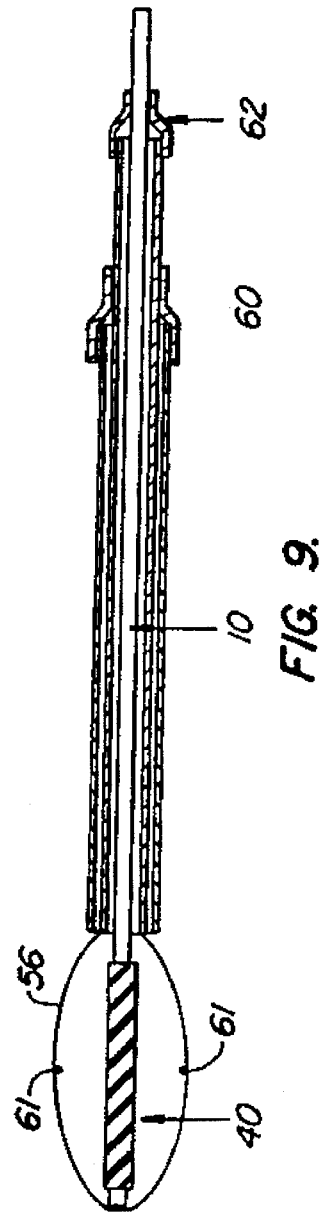

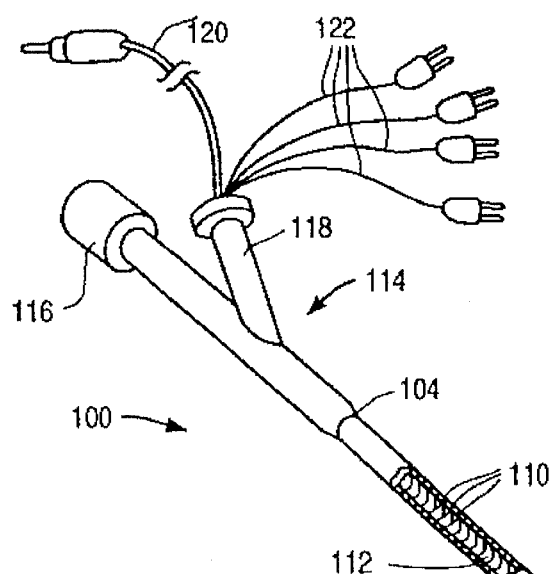
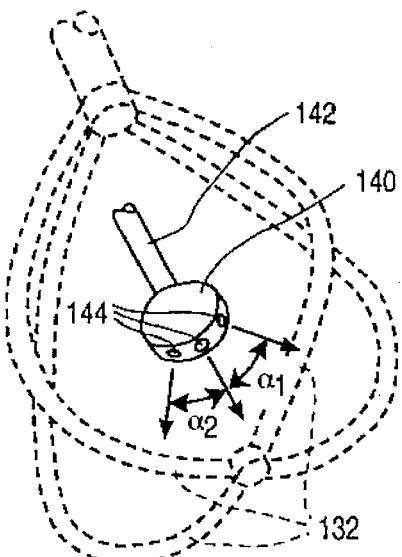
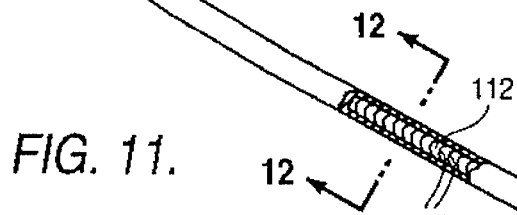
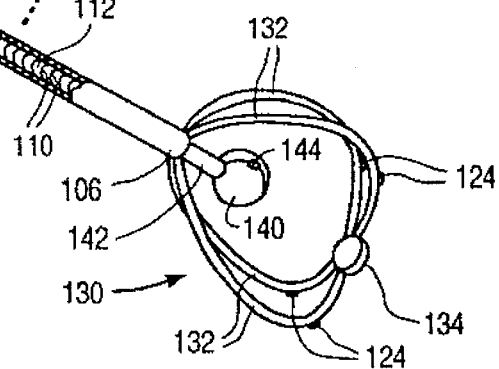
FIG. 11.
FIG. 14.
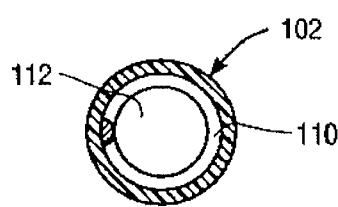
FIG. 12.
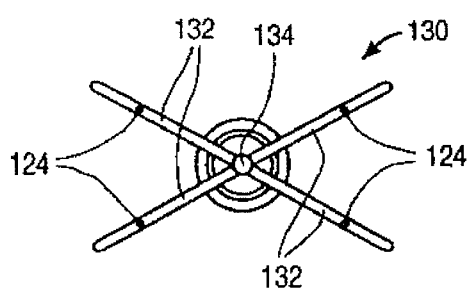
FIG. 13.

METHOD AND DEVICE FOR THERMAL ABLATION HAVING IMPROVED HEAT TRANSFER

BACKGROUND OF THE INVENTION

The present application is a continuation-in-part of application Ser. No. 08/073,639, filed on Jun. 7, 1993, now U.S. Pat. No. 5,433,708 which was a continuation of application Ser. No. 07/702,796, filed on May 17, 1991, now abandoned. The full disclosures of each of these references is hereby incorporated herein by reference.

FIELD OF THE INVENTION

The present invention relates generally to methods and apparatus for the thermal ablation of hollow body organs, such as the gallbladder and the uterus. In particular, the present invention relates to a catheter structure having a heating element extending through its central lumen and a method for inducing an oscillating flow of a heat transfer fluid past the heating element to enhance heat transfer to and temperature uniformity throughout the transfer medium.

In recent years, a variety of "minimally invasive" surgical procedures has been developed as alternatives to conventional "open" surgery. While minimally invasive surgical procedures have no fixed definition, they are generally characterized by use of specialized surgical tools in combination with visual or radiographic imaging techniques. The specialized tool is generally inserted through an open body orifice or a small surgical incision, and the tool is then positioned within the body using the imaging technique to allow manipulation of the organ or structure to be treated. A common example of least-invasive surgery is arthroscopic knee surgery, where penetration of the surgical tools is minimal. Less-accessible body organs, such as the heart and interior blood vessels, may be reached by specialized catheters which may be routed through the vascular system over relatively long distances. Exemplary of such vascular catheters are balloon dilatation catheters which are used to expand regions of stenosis within diseased blood vessels.

Of particular interest to the present invention are least-invasive and other surgical techniques which rely on a catheter to deliver heat to the interior of a hollow body organ. As described in detail in U.S. Pat. Nos. 5,045,056; 5,100,388; and 5,222,938, a catheter is used to deliver heat to necrose or ablate a diseased body organ, such as a gallbladder, uterus, appendix, kidney, or the like, as well as to occlude other body lumens, such as blood vessels. In each case, the heat is delivered by conduction through a thermal conduction medium from a heating element disposed on the catheter within the organ or blood vessel. The heat destroys the mucosa or endothelial lining of the organ or vessel, resulting in deactivation and eventual resorbtion of the organ or vessel.

The use of catheters having heating elements at their distal ends to deliver heat within a hollow body organ can be problematic in certain respects. First, heat distribution through the thermally conductive medium can be non-uniform, requiring an increase in the total amount of heat delivered in order to assure that the temperature of all portions of the mucosa are raised above the threshold level necessary to induce injury and necrosis. Such an increase in heat delivery, however, may raise the temperature of the other portions of the mucosa above a desired maximum. Such excessive heating can result in injury to adjacent body organs.

A related difficulty arises from the limited capacity of most catheters to deliver heat to the thermally-conductive medium. In order to deliver sufficient heat to remote portions of the mucosal wall, it may be necessary to raise the surface temperature of the heating element above a desired maximum. Excessive heat can result in fouling of the heating element as a result of coagulation and denaturing of blood and other proteins present. Such fouling, of course, further reduces the heat transfer capacity of the heating element.

In addition to heat transfer capacity and characteristics, conventional thermal heating catheters can have difficulty in transferring heat to remote locations within a hollow body organ. It will be appreciated that hollow body organs, such as the uterus and the gallbladder, are irregularly shaped and that portions of the interior lining of the hollow body lumen will be more remote from the heat delivery catheter than other portions. While heat delivery to these remote portions can be enhanced by thorough and repeated mixing of a heat transfer medium within the lumen, such mixing is not always completely effective. Thus, there can be instances where uneven heating of the lining of the hollow body lumen occurs. Such uneven heating is undesirable since overheating at any particular location can result in damage to underlying tissue structures and organs.

Even if temperature uniformity within the lumen of the hollow body organ is achieved, there may be differential heating of different areas of the organ lining. It will be appreciated that different areas of the organ may have different heat capacities and structures which can result in more or less rapid heating, particularly at different depths beneath the surface of the lining. Thus, it would be desirable to monitor temperature directly at the surface of the lining as well as at different depths beneath the surface of the lining in order to accurately predict and control the rate of thermal treatment and necrosis.

For these reasons, it would be desirable to provide improved methods and apparatus for delivering heat to the interior of hollow body organs. It would be particularly desirable to provide thermal ablation catheters having improved heat transfer characteristics, such as increased available heat transfer area, so that the surface temperature of a heating element can be maintained below a desired maximum level, typically being below about 100° C., preferably being below about 90° C. It is particularly desirable to provide catheters having increased heat transfer areas where the heat transfer surface is maintained as close to the end of the catheter which delivers the fluid as possible. The methods and apparatus should further provide for improved uniformity of heat distribution throughout the thermally conductive medium used to transfer heat from the catheter to the mucosal lining of the hollow body organ. Such improved heat transfer should even further reduce the surface temperature of the heating element as well as reducing the total amount of heat delivered to the body organ. The reduction in total heat will reduce the likelihood of unintentionally injuring adjacent tissue and body organs. The catheters of the present invention should have few or no moving parts and should be simple and reliable in design.

DESCRIPTION OF THE BACKGROUND ART

Catheters and methods for thermally assisted ablation of the gallbladder and other body organs are described in U.S. Pat. Nos. 5,045,056; 5,100,388; and 5,222,938, and in McGahan et al. (1992) Invest. Radiol. 27:1–7; and McGahan et al. (1994) Invest. Radiol. 29:355–360.

Catheters and methods for thermally assisted ablation of the uterus are described in U.S. Pat. Nos. 5,277,201 5,242,390 and 4,949,718; and Neuwirth et al. (1994) Obstet. Gynecol. 83:792–796.

U.S. Pat. No. 4,160,455, describes a bi-directional pump and unidirectional valve means for circulating a fluid through a housing containing a heating element. The entire housing is placed within a body cavity for effecting heat treatment of tumors. The device relies on forming a single high-speed outlet jet to agitate the fluid content of the organ. U.S. Pat. No. 4,979,948, describes a device having a radio frequency balloon electrode at its distal end for thermally destroying the mucosal layer of a body organ, such as the gallbladder. U.S. Pat. Nos. 4,655,744; 4,723,941; 4,755,167; 4,758,596; 4,793,776; and Australian published application A-71786/87, describe improved methods for performing chemical cholecystectomy where a stone dissolving agent is oscillated in and out of a body area.

Coleman, *Non-Surgical Ablation of the Gallbladder*, Proc. 1988 SCVIR, pp 214–219, is a review article discussing various techniques for non-surgical gallbladder ablation, including the work of Salomonowitz and of Getrajdman relating to the introduction of an externally heated medium to induce fibrosis of the gallbladder. The article further presents data demonstrating thermal ablation of a dog's gallbladder after open surgical injection of hot contrast media. The work of Salomonowitz is described in Salomonowitz et al. (1984) Arch. Surg. 119:725–729. The work of Getrajdman is described in Getrajdman et al. (1985) Invest. Radiol. 20:393–398 and Getrajdman et al. (1986) Invest. Radiol. 21:400–403. The use of sclerosing agents to induce gallbladder fibrosis is described in Remley et al. (1986) Invest. Radiol. 21:396–399. See also Becker et al. (1988) Radiology 167:63–68; Becker et al. (1989) Radiology 171:235–240; and Becker et al. (1989) Work in Progress Paper #1354, RSNA Meeting, November 1989. U.S. Pat. No. 4,160,455, describes a device for internally heating a body cavity for therapy, where the heat is intended to inhibit the growth of tumor cells. German Patent 37 25 691 describes a catheter combining a heater at its distal tip and a balloon proximate the heater, where the heater is not directly exposed to the fluid environment surrounding the catheter tip. U.S. Pat. No. 4,869,248, describes a thermal ablation catheter having a resistive heating loop at its distal end. Other patent documents describing heated or cooled catheters include U.S. Pat. Nos. 4,676,258; 4,638,436; 4,469,103; 4,375,220; 3,901,224; USSR 1329-781-A; and USSR 281489.

SUMMARY OF THE INVENTION

The present invention comprises apparatus and methods for thermally treating a hollow body organ, such as a uterus, gallbladder, appendix, kidney, esophagus, and the like. The apparatus comprises a catheter having an elongate member or body with a proximal end, a distal end, and a lumen extending between said ends. A heating element is provided on the elongate member or body, preferably within the lumen so that fluid passing through the lumen, in either direction, can be heated by the heating element. Thermal treatment can be effected by introducing the catheter into the hollow body organ, either percutaneously or through a natural body orifice, so that a distal end of the lumen lies within the interior of the body organ. A thermally conductive heat transfer fluid within the interior of the organ is heated by inducing an oscillatory flow between the catheter lumen and the organ in order to provide the heat necessary for the thermal treatment.

In a first aspect, the present invention comprises disposition of the heating element within the lumen of the elongate member or body of the catheter. Usually, the heating element will be disposed within or over at least the distal-most 1 cm of the lumen. Preferably, the heating element will be distributed over a discrete length of the lumen, up to and including the entire length of the lumen, so that the available heat transfer area can be maximized. In the exemplary embodiment, the heating element is a wire coil.

In a second aspect, the present invention comprises a flow directing element disposed at the distal end of the lumen in the elongate member or body of the catheter. The flow directing element preferably includes at least two ports for directing fluid in at least two different directions. For example, the two ports may be directed to create two flow streams which diverge from each other at an angle from about 60° to 150°. Preferably, a cage structure will be formed over the flow directing element, where the cage structure is adapted to open or expand the interior of the hollow body organ to create and maintain an open volume for thermal treatment. The cage structure is usually expansible so that it can be introduced in a collapsed configuration and thereafter expanded within the hollow body organ to an enlarged configuration which maintains the desired heating volume. In the exemplary embodiment, the cage structure is resilient so that it assumes the collapsed configuration when constrained within an introducing cannula or sheath and reassumes the expanded configuration when released therefrom.

In a third aspect, the present invention comprises a thermal treatment catheter having a cage structure at the distal end of its elongate member or body. The cage structure is configured to engage the interior surfaces or walls, typically the endothelial or mucosal linings, of the hollow body organ being treated, usually being expansible from a collapsed to expanded configuration as described above. At least one temperature sensing element will be provided on the exterior of the cage structure so that the temperature sensing element will directly contact the interior wall of the hollow body organ so that the temperature of the wall (as opposed to the temperature of free liquid within the hollow body organ) may be measured. In a preferred aspect, the temperature sensor will be located on a penetrating element which, when the cage engages the wall of the hollow body organ, will penetrate beneath the surface of the hollow body organ to measure temperature at a depth of at least 1 mm, usually being in the range from 1 mm to 20 mm, preferably being from 2 mm to 6 mm. The ability to measure temperature beneath the surface of the hollow body organ is particularly desirable since it is the temperature below the surface of the lining which most accurately indicates progress in the treatment protocol, e.g., whether or not the organ lining has been ablated and whether underlying organ and tissue structures are at risk of injury.

According to a first aspect of the method of the present invention, a catheter is introduced percutaneously or through a natural orifice into the hollow body organ to be treated. An oscillatory flow of thermally conductive fluid is induced between the catheter and the interior of the hollow body organ, and heat is introduced to the fluid as it flows in and out of the catheter lumen. Preferably, temperature of the thermally conductive fluid will be maintained within the range from 45° C. to 90° C. within the lumen, and the fluid will be aspirated and expelled at volumes in the range from 0.1 ml to 5 ml and at frequencies in the range from 10 to 60 cycles/minute. Preferably, fluid flowing from the catheter is directed at particular regions of the body lumen, such as the cornua regions of the uterus.

In a second aspect of the method of the present invention, heat is transferred to a lumen of the hollow body organ being treated while temperature of the organ is measured at or near a surface of the surrounding endometrial or mucosal lining. The amount of heat transferred to the organ is controlled to maintain the measured temperature within a desired range. Preferably, the temperature is measured at a depth beneath the lining of at least 1 mm, usually being in the range from 1 mm to 20 mm more preferably being from 2 mm to 6 mm. For treatment of the uterus, the temperature is maintained within the range from 60° C. to 90° C. For treatment of the gallbladder, the temperature is maintained within the range from 50° C. to 60° C.

BRIEF DESCRIPTION OF THE DRAWINGS

FIG. 1 is a perspective view of a thermal ablation catheter constructed in accordance with the principles of the present invention.

FIG. 2 is a cross-sectional view taken along line 2—2 of FIG. 1.

FIG. 3 is a cross-sectional view taken along line 3—3 of FIG. 1.

FIG. 7 illustrates an introducer sheath having an expandable cage at its distal end which is useful for introducing the thermal ablation catheter of the present invention, shown with its expandable cage in a collapsed configuration.

FIG. 8 illustrates the introducer sheath of FIG. 7, shown with its expandable cage in its expanded configuration.

FIG. 9 illustrates the introducer sheath of FIG. 8, shown with the thermal ablation catheter present therein.

FIG. 11 is a perspective view of an alternative embodiment of a thermal treatment catheter constructed in accordance with the principals of the present invention, wherein a heating element is distributed over a central lumen of the catheter.

FIG. 12 is a cross-sectional view taken along line 12—12 of FIG. 11.

FIG. 13 is an end view of the catheter of FIG. 11.

FIG. 14 is a detailed view of a flow distribution element located at the distal end of the catheter FIG. 11, shown with an expandable cage structure in broken line.

DESCRIPTION OF THE SPECIFIC EMBODIMENTS

Figure 4:
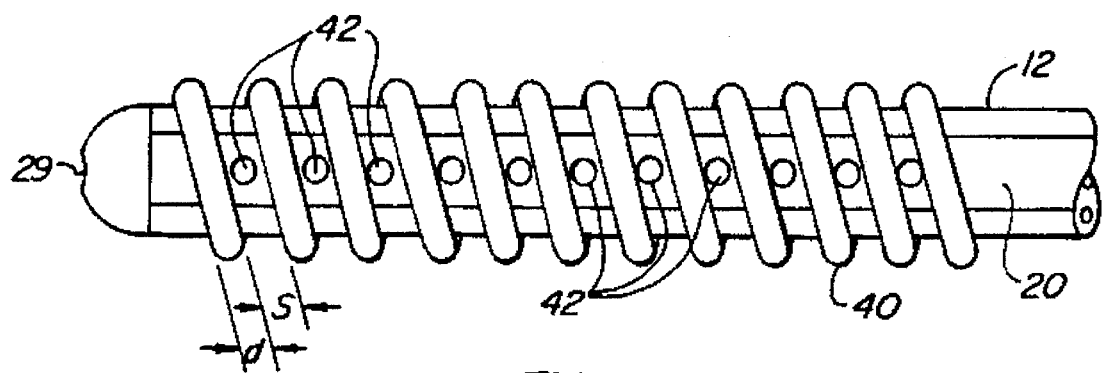
FIG. 4 is a detailed elevational view of the distal end of the catheter of FIG. 1.

According to the present invention, apparatus and methods are provided for heating the interior of a wide variety of hollow body organs, cavities, ducts, and passages, particularly including those which have an epithelial lining, endothelial lining, endometrial lining mucous membrane, or other internal surface which may be thermally injured to inactivate the organ and usually to induce necrosis and subsequent fibrosis of the organ itself. Alternatively, the present invention may be used to provide thermal therapy where the temperature of the surrounding tissue is raised, particularly in the treatment of solid tumors and other neoplastic diseases. Exemplary hollow body organs and cavities include the gallbladder, the uterus, the appendix, the kidney, and the like. Exemplary hollow body passages and ducts include blood vessels, fistulas, and the like. When the intent is to inactivate, the hollow body organ will usually be diseased or in some way abnormal prior to treatment according to the present invention. When the desire is to thermally treat surrounding tissue, an organ or passage may serve merely as an access route. In other cases, it may be desirable to ablate and destroy apparently healthy body organs or parts in order to achieve a desired purpose, e.g., blockage of a blood vessel in a varicocele procedure. For convenience hereinafter, the phrase "hollow body organ" is intended to embrace hollow body organs, hollow body passages and hollow body cavities.

The catheter of the present invention comprises an elongate member having proximal and distal ends. The elongate member may be flexible or rigid, although flexible catheters are preferred for most applications. The length of the catheter will vary depending on the application, typically being from about 10 cm to 100 cm, usually from about 10 cm to 50 cm, and more usually from about 10 cm to 30 cm, although longer structures will usually be provided for intravascular applications. The diameter of the catheter will also vary depending on the application, typically being at least 1 mm, usually being from 2 mm to 10 mm, with smaller diameters being necessary to access smaller targets and pass through smaller orifices, lumens, and the like. For treatment of gallbladders, the catheter will typically have a length from 8 cm to 15 cm, and an outer diameter in the range from 2 mm to 6 mm. For treatment of the uterus, the catheter will typically have a length from 20 cm to 30 cm typically being about 25 cm, with an outside diameter from 4 mm to 8 mm.

Rigid elongate members may be formed from metals, typically stainless steel, rigid plastics, and the like, while flexible elongate members will typically be formed from extruded organic polymers, such as silicone rubber, polyurethane, polyvinyl chloride, nylon, and the like.

Elongate members will typically include a multiplicity of lumens to provide for fluid communication between the proximal end (which remains outside the patient) to the distal end (present inside the patient during treatment). Normally, a lumen will be provided for delivering and aspirating the thermally conductive medium to the hollow body organ. Additional lumens may be provided for delivery of the catheter over a movable guide wire, for venting the hollow body organ while the thermally conductive medium is being delivered, for electrical power and signal connections, and the like.

A first type of heating means for raising the temperature of the fluid environment surrounding the distal end of the catheter will be provided at or near the distal tip of the elongate member typically being within about 10 cm of the tip, more typically being within about 5 cm. The heating means will provide a heated surface for heating fluid surrounding the catheter tip, usually including a resistive heater element. Preferably, the heated surface of the heating means will be exposed directly to the environment surrounding the catheter, with little or no insulation covering the surface, in order to enhance heat transfer. The heating means will be directly exposed to its surrounding environment and will not be enclosed in a housing or other structure which substantially impedes direct heat exchange with surrounding fluid in the body organ.

The heated surface of the first type of heating means will be located over an extended axial length at or near the distal tip of the elongated member. The length will usually be from about 1 cm to 8 cm, more usually being about 2 cm to 6 cm, and most usually being about 1.5 to 4 cm. The heated surface will be suspended over or spaced-apart from the exterior surface of the elongate member to define a circulation region therebetween. As described hereinafter, the thermally conductive fluid will usually be passed from the central lumen into the circulation region to enhance heating thereof. In particular, by suspending the heating element, additional heating surface of the element is exposed to the thermally conductive medium as it is distributed from the catheter.

The heating element will be a permeable or perforate structure in order to increase the total surface area to enhance heat transfer. For example, a cylindrical mesh or other perforate cylindrical structure may find use as a heating element, where the thermally conductive fluid can pass through the interstices or apertures of the structure.

A preferred heating element is a coiled structure where an elongate heating element, e.g., a wire, is wrapped in a helix about a supporting structure at the distal end of the elongate member. Successive turns of the helical coil are spaced-apart to permit flow of the thermally conductive medium therethrough and to minimize the thermal effect of adjacent turns on each other. By suspending the heating element away from the elongate member, the exposed surface area of the heating element is maximized, with only the suspension points being blocked. Usually, the heating element will be a resistance heating wire having a diameter in the range from about 0.05 mm to 0.25 mm, usually from about 0.1 mm to 0.15 mm, where spacing between successive windings of the coil are from about 0.5 to 2 diameters. The number of turns in the heating element may vary, typically being from about 3 to 8 turns/mm, more typically being from about 4.5 to 5.5 turns/mm, depending in part on the total length which is to be covered, the linear electrical resistance of the wire, and the desired heat transfer rate.

The means for suspending the heating element from the surface of the elongate member may take a variety of forms. For example, it would be possible to form a plurality of discrete support posts on the surface of the elongate member. Alternatively, the coil heating element could be shaped so that it defines integral support posts in its own structure. Preferably, the suspension means will comprise a plurality of axial ribs formed in the elongate member itself. At least three ribs will be employed, with troughs between adjacent ribs defining the circulation region between the heater and the elongate member. The use of ribs is preferred since they are relatively easy to fabricate, e.g., by extrusion or other techniques.

The thermally conductive medium is introduced through a lumen which extends from the proximal end to distal end of the elongate member. The lumen will open into a plurality of distribution ports at the distal end of the elongate member which permits flow of the thermally conductive medium into and through the recirculation region between the member and the heating element. In this way, heat transfer between the medium being introduced and the heating element can be maximized.

Rather than exposing a heating element directly to the fluid environment by exposing the heating element on an exterior surface of the catheter, it will in many cases be preferable to provide a heating element within the lumen of the catheter which carries the thermally conductive fluid. In this way, the thermally conductive fluid will contact the heating element as it is introduced and/or oscillated between the catheter lumen and the interior of the hollow body organ being treated. Such heating elements located within the catheter lumen may be discrete unit heaters, i.e., located over a short distance within the catheter lumen, such as 1 cm or less, but will preferably be distributed over an extended length of the catheter lumen, usually greater than 5 cm, preferably greater than 10 cm, and frequently over the entire length of the catheter lumen. The use of such longer, distributed heaters increases the available heat transfer area for delivering heat into the thermally conductive medium, thus allowing the heating elements to operate at a lower temperature while achieving sufficient heat flux. A presently preferred heating element located within the catheter lumen comprises an electrical resistance element disposed over the entire surface, usually a wire coil lining the entire lumen of the catheter. Such coils may generally be formed as described above for the exterior heating elements.

The catheter of the present invention will frequently be employed as part of a thermal ablation system comprising, in addition to the catheter, a power supply connected to the heater and a means for inducing an oscillatory flow of thermally conductive medium past the resistive heating element. The power supply will typically include means for controlling the temperature to which the thermally conductive medium is heated by the heating means. Such a temperature control system may comprise a feedback controller where a temperature sensing element (typically one or more thermocouples or thermistors) is mounted on the catheter and/or an associated introducer sheath (as described in more detail hereinbelow) at a location chosen to accurately measure the heated environment surrounding the catheter, and the energy delivered to the heating means is regulated based on the measured temperature of the medium. Preferably, the temperature control system will include temperature sensing element(s) mounted on an expandable cage at the distal end of the introducer sheath. Such element(s) will be in close proximity to the wall of the organ or duct which is being treated, where the temperature is most critical.

The means for inducing an oscillatory flow of thermally conductive medium will typically include a syringe or other pump mechanism which can be connected to the medium introduction lumen in the catheter. Thus by driving the syringe or pump with a preselected stroke and frequency, a desired volume of the thermally conductive medium can be caused to alternately be aspirated and expelled by the catheter. In this way, heat transfer and uniform heat distribution of the system can be enhanced.

The thermal ablation system optionally includes the introducer sheath having an expandable structure or cage near its distal end. The introducer sheath will be used to introduce the thermal ablation catheter and to expand the portion of the hollow body organ in which the heating element of the catheter is positioned. The expanded cage can thus both protect the organ wall from direct contact with the heating element and position the heating element and optionally fluid diffuser near the center of the organ so that heat is uniformly distributed to all portions of the organ.

The cage structure on the introducer sheath preferably comprises a plurality of axially aligned fingers which can be introduced in a collapsed configuration and expanded within the hollow body organ or duct in order to provide the desired expanded cage structure. Such a cage, of course, will be substantially open so that the inner wall of the organ or duct will be completely exposed to the thermally conductive medium which is being heated by the catheter. The fingers may be spring-loaded to open when they are released within the body organ or duct, or a separate means may be provided for mechanically causing the opening. Other designs, such as the use of shape and heat memory alloys, may also find use. Regardless of the particular construction, it will be particularly preferred to provide one or more temperature sensing elements on at least some of the finger elements which form the expandable cage. Desirably, the temperature sensing elements will be located at the point(s) of maximum radial expansion on the cage. In this way, the temperature sensing elements will be located immediately adjacent to the inner wall of the hollow body organ during the thermal treatment procedure and will thus be able to accurately measure the localized temperature at the point of thermal impact.

In an alternative embodiment of the present invention, a cage structure generally as described above may be mounted directly on the thermal delivery catheter. In an exemplary embodiment, the cage structure comprises a plurality of resilient elements or rods which, in an unconstrained configuration, define a shape which nests within the hollow body organ being treated. The catheter and caged structure can be introduced through a suitable cannula or sheath with the cage structure in a collapsed configuration. After the cage structure passes out of the cannula or sheath, the cage structure will expand to its unconstrained configuration, preferably engaging the interior wall of the hollow body organ to open the organ to receive the thermally conductive medium. Use of such resilient cage structures, however, is not essential, and the present invention encompasses the use of mechanical structures which may be positively expanded and collapsed using appropriate mechanical linkages in order to facilitate introduction of the cage structure and subsequent enlargement of the cage structure to the desired final configuration.

In a further preferred aspect of the present invention, a flow directing element may be mounted on the thermal treatment catheter in order to direct flow of the thermally conductive medium as it is expelled from the lumen of the catheter. Preferably, such flow directing elements will be located within an expansible cage structure, as described above, where the cage structure fixes the position of the distal end of the catheter body within the hollow body organ or lumen and facilitates proper alignment of the flow directing element within the hollow body organ being treated. The flow directing element will usually include at least two ports, wherein each port is oriented in a predetermined manner in order to direct heated fluid toward a region of the hollow body organ which might otherwise receive insufficient heating. Such flow directing elements are particularly useful with catheters having internal heating elements, where the fluid expelled from the catheter will be heated to the maximum desirable temperature. In a particularly preferred aspect, the flow directing element includes at least two ports which diverge from each other at an angle in the range from 30° to 180° usually between 60° and 150° which are oriented to direct fluid against the cornua regions of the uterus which is being treated.

In a further preferred aspect of the present invention, temperature sensors on the expandable cage will comprise penetrating elements which, when engaged against an adjacent hollow body lining, will dispose the temperature sensor at a preselected depth beneath the surface of the lining. Usually, the depth will be in the range from 1 mm to 20 mm, preferably being between 2 mm and 6 mm.

The method of the present invention relies on introducing the thermally conductive medium into the interior of the hollow body organ in such a way that the organ is filled with the medium and the medium is in good thermal contact with substantially the entire interior surface of the organ. The heating element then transfers heat directly to the thermally conductive medium which in turn transfers the heat to the organ wall by convection. In this way, by heating the medium as will be described hereinafter, the temperature of the epithelial lining, endothelial lining, endometrial lining, or mucous membrane of the body organ can be raised to a preselected temperature for a preselected minimum time period in order to permanently injure the lining and/or deactivate the organ. In the case of gallbladder treatment, the gallbladder will usually be treated at a temperature and for a time sufficient to ablate the organ and cause resorption. In the case of uterine treatment, it will often be sufficient to injure the endometrial lining so that scar tissue is formed, thus presenting uterine bleeding which is often the condition being treated. The thermally conductive medium can be virtually any physiologically-compatible liquid, solution, slurry, gel, or the like, which can be percutaneously or directly introduced into the interior of the hollow body organ. Exemplary thermally conductive media include water, normal saline, contrast media, physiological irrigating solution, and the like. Alternatively, natural body fluids within the organ can provide a portion or all of the thermally conductive fluid.

Thermal treatment according to the present invention includes but is not limited to thermal ablation. As used herein, the term "ablation" means any injury or damage to the hollow body organ and/or connecting ducts and body passages which results in deactivation of the function of the organ, usually resulting in necrosis and eventual resorption of the organ. The resorption will typically occur over an extended period of weeks, months, or longer. Other thermal treatment, particularly of the endometrial ling of the uterus, will result in scar formation only, not causing necrosis or resorption of the organ.

The thermally conductive medium may be introduced to the interior of the hollow body organ at a temperature below that which will have a deleterious effect on the tissue and organs surrounding the hollow body organ being treated. The temperature will usually be below about 42° C., more usually being at body temperature (37° C.) or room temperature (about 20° C.). In some cases, however, it may be desirable to introduce the contrast medium above body temperature, usually in the range from about 37° C. to 42° C., in order to shorten the time necessary to raise the temperature of the medium to the treatment temperature, discussed hereinafter. In other cases, it may be desirable to introduce the medium at or near the treatment temperature (as described below), in which cases it will be desirable to place thermal insulation over-at least a portion of the catheter and/or access cannula to protect tissue surrounding the catheter body.

In order to induce necrosis of the epithelial lining, endothelial lining endometrial lining, or mucous membrane of the hollow body organ, the temperature of the thermally conductive medium will be raised and/or maintained above a threshold level which results in injury to the endothelial lining, epithelial lining, endometrial lining, or mucous membrane. The threshold temperature will generally be above 42° C., usually being in the range from 45° C. to 90° C., more usually being in the range from 50° C. to 85° C., and preferably being in the range from about 54° C. to 85° C. Preferred temperatures for the treatment of the gallbladder and the uterus are set forth above. Depending on the precise temperature employed and on the nature of the particular organ being treated, the thermally conductive medium will be maintained above the threshold temperature for a period of time in the range from about 1 to 60 minutes, usually being in the range from about 5 to 40 minutes, and preferably being in the range from about 15 to 35 minutes. Usually, the temperature of the thermally conductive medium will be raised as rapidly as possible and maintained at a substantially constant treatment temperature for the desired treatment period. Alternatively, the treatment temperature may vary or be varied during the treatment period with the total treatment time being adjusted to take the variation in organ size, heat transfer characteristics, thermally conductive medium perfusion rate, temperature limitations, and the like into account.

After the thermally conductive medium has been introduced and heat transfer initiated through the heating element, the method of the present invention relies on alternately aspirating and expelling incremental volumes of the medium through the catheter. Such an oscillatory flow has been found to significantly enhance temperature uniformity (through mixing of the medium) as well as heat transfer (through continuous reversing flow of medium through and past the heating element). Both the enhanced temperature uniformity and the increased heat transfer rate allow the thermal ablation procedures to reduce the total amount of heat delivered to the organ as well as the temperature of the heating surfaces required to deliver that amount of heat.

The volume which is aspirated will usually be substantially the same as the volume which is expelled. Typically, the aspirated and expelled volumes will be in the range from about 0.1ml to 5 ml, more usually being from about 1 ml to 2.5 ml, and the frequency of oscillation will be in the range from about 10 to 60 cycles/minute, typically being in the range from about 30 to 50 cycles/minute.

In a preferred aspect of the method of the present invention, temperature of the tissue being treated will be monitored and controlled, rather than monitoring of the temperature of the thermally conductive fluid. In a first embodiment of this preferred aspect, temperature is monitored using one or more temperature sensors disposed against the interior lining of the hollow body organ. Conveniently, such temperature sensors may be mounted on the distal cage structure on the catheter, preferably with two or more sensors being strategically located to monitor different portions of the organ which would be expected to be heated at different rates. In a preferred embodiment, the tissue temperature will be monitored at a preselected depth below the interior surface of the hollow body organ. Such monitoring can be performed using temperature probes which penetrate the tissue to the desired depth, typically in the range from 1 mm to 20 mm, preferably in the range from 2 mm to 6 mm. In an exemplary case, the temperature probes are penetrating elements mounted on the expansible cage structure which is on the thermal treatment catheter.

After the hollow body organ has been treated with the heated thermally conductive medium at a temperature and for a time sufficient to deactivate the body organ and/or induce necrosis of the endothelial lining or mucous membrane of the organ, the thermal energy being delivered to the medium will be terminated. The thermally conductive medium may then be aspirated from the hollow body organ, typically using the same catheter which was employed to deliver the medium and raise the temperature of the medium as described above. Usually, however, the thermally conductive medium will not be aspirated until the temperature has decreased sufficiently so that its withdrawal will not expose tissues and organs surrounding the catheter to risk. Normally the withdrawal temperature will be below about 42° C., preferably being below about 40° C. Alternatively, the thermally conductive medium can be left within the hollow body organ where it will be resorbed or eliminated by normal physiological processes.

Referring now to FIGS. 1–4, the construction of a catheter 10 constructed in accordance with the principles of the present invention will be described. The catheter 10 includes an elongate element or body 12 having a proximal end 14 and a distal end 16. The catheter body 12 has a cross-sectional profile including three rib elements 18 separated by three trough regions 20. The elongate body 12 further includes four lumens 22, 24, 26, and 28 extending generally from the proximal end 14 to or close to the distal end 16.

The elongate catheter body 12, as illustrated, is shown to be flexible along substantially its entire length. Optionally, portions of the catheter body 12 may be constructed from rigid or semi-rigid materials, for a desired purpose. For example, it may be necessary or desirable to provide a rigid supporting member for the heater having higher or different heat transfer characteristics than the rest of the elongate catheter body. Metals or other heat conductive materials might find use in such designs. Other reasons for departing from the generally flexible nature of the catheter body 12 may occur to those skilled in the art while remaining within the scope of the present invention.

A pair of temperature sensor leads 30 enter the first lumen 22 near the distal end 14 of the catheter body 12 and terminate at external temperature sensors 32 at the distal end 16. Of course, the temperature sensor leads 30 will not be necessary when temperature sensing elements are provided only on the expandable cage of the introducer sheath, as described in more detail hereinafter. Similarly, a first power lead 34 enters lumen 24 at the proximal end of the catheter while a second power lead 36 enters lumen 26 at the proximal end of the catheter. The power leads 34 and 36 are connected to a heating coil 40 wrapped about and extended axial length near the distal tip of the catheter 10. When not employed for temperature sensor leads, lumen 22 may be used as an auxiliary perfusion and/or aspiration lumen.

Central lumen 28 is connected to a plurality of radial apertures 42 which open into the three trough regions 20 which are located beneath the heating coil 40. In this way, the thermally conductive medium can be introduced through a connector 46 at the proximal end of the catheter 10 and in turn be distributed through the various radial apertures 42 which open into a circulation region defined by the trough regions 20 of the catheter body 12. Central lumen 28 terminates in a port 29 located at the distal tip of the catheter body 12. Usually, the diameter of the port 29 will be smaller than that of the lumen 28 so that there will be a close fit about the center wire (not illustrated) which is used for introducing the catheter 10. Such a close fit inhibits flow of the thermally conductive medium through the port 29, which flow is generally undesirable since it bypasses the heating element 40. Flow through the port 29, however, does contribute to the mixing capability of the catheter 10 and to a limited extent may be acceptable or desirable.

Referring now in particular to FIG. 3, the heating coil 40 is wrapped around the catheter body 10 so that it is suspended on the axial ribs 18. Portions of the heating coil 40 which are between the axial ribs 18 are thus completely exposed to the surrounding environment. In particular, the wires are exposed to the thermally conductive medium as it is released or expelled through the axial apertures 42 as well as when it is aspirated back into the catheter through said apertures. Heat transfer or flux from the heating coil 40 will be a compromise between maximizing the total wire length and providing sufficient spacing between adjacent turns of the wire to increase exposure and permit free flow of thermally conductive medium therethrough. That is, the total wire length (which increases the total surface area of the wire) is increased by having a higher number of turns on the catheter. Too high a turn density, however, limits both the effective exposed area of each turn and limits the flow of thermally conductive medium through the coil 40. An optimum compromise heat transfer can be achieved when the spacing s (FIG. 4) between adjacent turns of the coil 40 is equal to from about 0.5 to 2 times the wire diameter d. For catheters having diameters in the range from about 1.5 mm to 3 mm, the wire diameter will usually be in the range from about 0.05 mm to 0.75 mm, with the spacing between adjacent turns of the coil being from about 0.025 mm to 0.25 mm.

Figure 5:
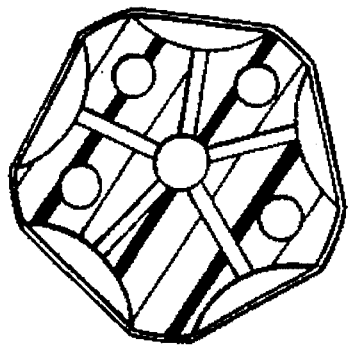
FIGS. 5 and 6 illustrate alternate cross-sections which would be useful in the construction of catheters according to the present invention.
Figure 6:
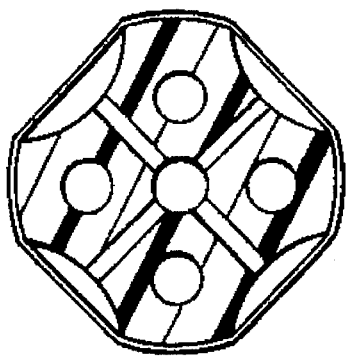

Referring now to FIGS. 5 and 6, alternate catheter body cross sections having different numbers of axial ribs are illustrated. The number of axial ribs is not critical, but it will be appreciated that at least three ribs will usually be required.

Referring now to FIG. 7, an introducer sheath 50 useful for inserting the thermal ablation catheter 10 into a variety of hollow body organs, such as the gallbladder, will be illustrated. The introducer sheath 50 includes an outer sheath member 52 and an inner sheath member 54. The inner sheath member 54 includes an expandable cage 56 at its distal end and a centering wire 58 extending throughout its length. The outer sheath 52 and inner sheath 54 will be configured as nested tubes which are capable of sliding relative to each other. The tubes may be rigid or flexible, usually being flexible to facilitate introduction through relatively tortuous paths.

The cage 56 includes a plurality of resilient fingers 57 (only two are illustrated) which are constrained in a collapsed configuration within the distal end of outer sheath member 52. Usually, although not necessarily, the individual fingers 57 will be connected together at their distal ends so that, when released from the outer sheath 52, they will spring into the expanded configuration illustrated in FIG. 8. It would also be possible to leave the individual fingers 57 unconnected at their distal end so that they remain free to expand away from each other. The cage 56 may also be configured so that it is expanded by pulling proximally on the centering wire 58 to axially compress the cage, forcing its radial expansion. A variety of other specific designs will be apparent to those skilled in the art. It is critical only that the cage 56 be expandable within the target body organ and that, when expanded, it cover or block a minimum area of the inner surface of the body organ.

The introducer sheath 50 will be inserted into a hollow body organ, typically through adjacent passages and ducts in a conventional manner, with the expandable cage 56 in a collapsed configuration held within the outer sheath 52. Once the introducer sheath is in position, the outer sheath member 52 will be translated relative to the inner sheath member 54 so that the cage 56 is freed to assume its expanded configuration, as illustrated in FIG. 8. Usually, a seal member 60 will be provided to seal against the outer sheath member.

Temperature sensors 61 may be disposed on at least some of the fingers 57 of the expandable cage 56. Preferably, at least two fingers 57 will include at least one temperature sensor 61. More preferably, at least one sensor will be located at the point of maximum expansion as illustrated for sensors 61 in FIGS. 8 and 9. In this way, the temperature sensors 61 will be located immediately adjacent to the endothelium or mucosa of the hollow body organ during treatment.

Once in position with the cage 56 expanded, the thermal ablation catheter 10 can be introduced over the centering wire 58 so that the heating element 40 is positioned within the expanded cage 56. In this way, the heating element 40 can be optimally positioned within the hollow body organ and direct contact between the heating element and the interior surfaces of the organ prevented. Usually, a second seal 62 will be provided on the catheter 10 in order to seal against the proximal end of the inner sheath 54.

Figure 10:
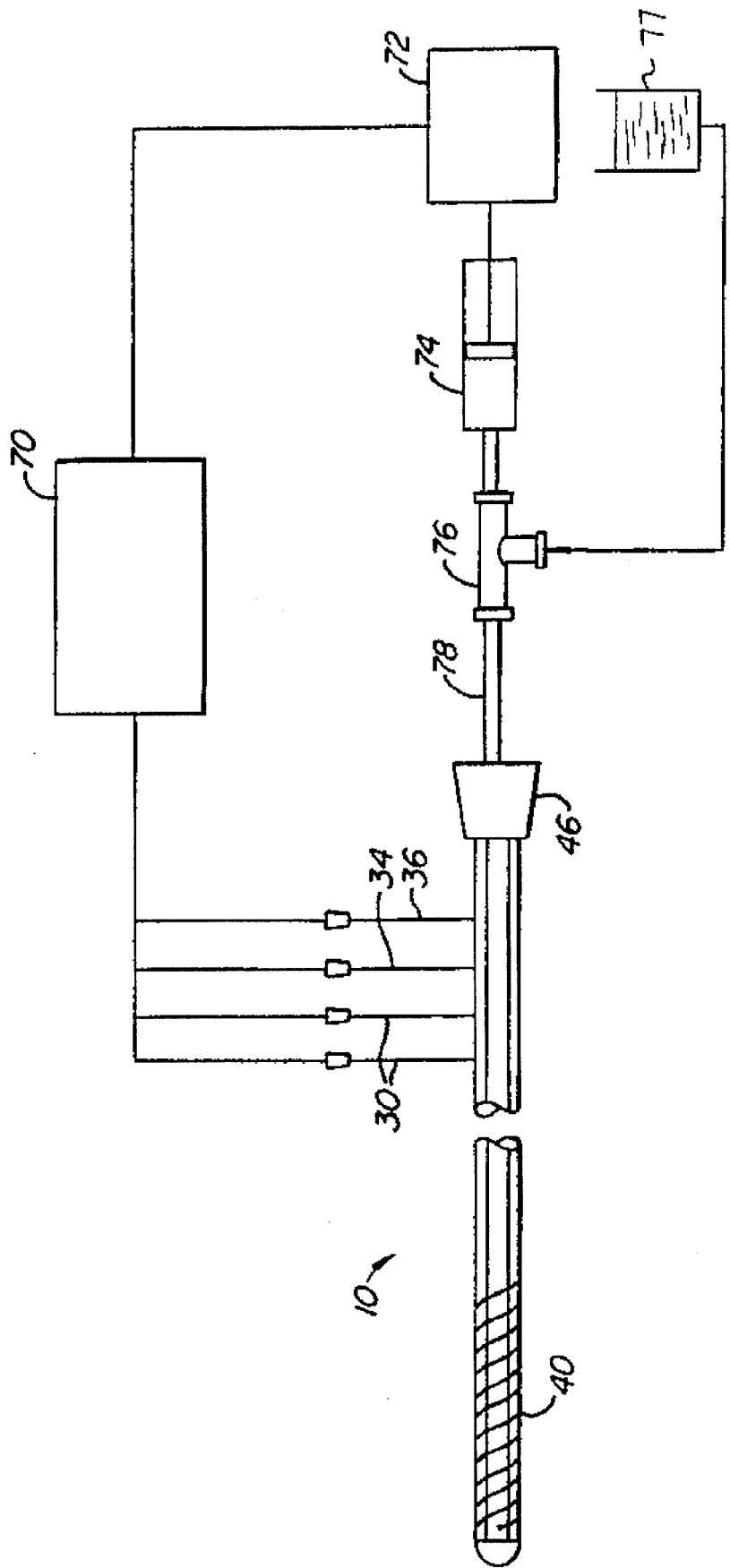
FIG. 10 is a schematic illustration of a system for heating and pumping a thermally conductive medium through the catheter of FIG. 1.

Referring now to FIG. 10, a system for connecting and operating the thermal ablation catheter 10 is illustrated. The system includes a power supply and controller 70 which is connected to the sensor leads 30 and power leads 34 and 36. The power supply and controller may be connected to a mechanical actuator 72 which drives a syringe assembly 74 to create a reciprocating pump mechanism. Alternatively, the mechanical drive may be separately actuated and controlled. The syringe 74, in turn, is connected to a three-way valve 76 which permits the introduction of the thermally conductive medium from a reservoir 77 into connecting tube 78. Connecting tube 78, in turn, is connected to the hub connector 46 on the thermal ablation catheter 10. In this way, after filling the hollow body organ with thermally conductive fluid, the valve 76 can optionally be switched to connect the syringe mechanism 74 and the desired oscillating flow of medium induced by starting the actuator 72. The desired volume, frequency, and the like, can be controlled through the power supply and control system 70 or by independent controls within the actuator 72 itself.

Preferably, the reservoir 77 will be open to the atmosphere, and the level of liquid therein will be disposed above the valve 76 and catheter 10 by a distance to provide a desired constant fluid pressure within the organ being treated, usually in the range from about 10 mmHG to 60 mmHG. The use of an open reservoir has a number of advantages. It provides a bleed path for releasing entrapped air and other gases from the oscillating thermally conductive medium. It also protects against accidental over pressure from the syringe assembly 74. Additionally, the reservoir assures that there will be sufficient fluid to maintain the desired base line fluid pressure within the organ being treated and provides a visual indicator of fluid volume and mixing efficiency.

The power to the heating coil 40 will be controlled to achieve a desired temperature, based on the temperature sensors 32 and/or 61. Usually, the fluid temperature will be in the range from about 53° C. to 60° C.

The catheter 10 may be introduced to a hollow body organ, such as the gallbladder, by techniques described in co-pending application Ser. Nos. 07/407,839; 07/529,077; and 07/551,971; the disclosures of which have previously been incorporated herein by reference.

For thermal ablation of the gallbladder, the optimum temperature of the medium will be from about 54° C. to 60° C. (usually corresponding to a heating element surface temperature of from about 70° C. to 90° C.), the optimum oscillation frequency will be from about 10 to 50 cycles/ minute, the oscillation volume from about 0.1 ml to 2.5 ml, and the total treatment time from about 15 minutes to 35 minutes.

Referring now to FIGS. 11–14, the construction of an alternative embodiment of a catheter 100 constructed in accordance with the principles of the present invention will be described. The catheter 100 includes an elongate element or body 102 having a proximal end 104 and a distal end 106. The catheter body 102 is tubular having a wire coil heating element 110 formed over an axial lumen 112 thereof. A proximal housing 114, typically in the form of a conventional Y-connector, includes a proximal port 116 for connection to a source of thermally conductive fluid, such as a combined power supply and oscillatory pump, as illustrated in FIG. 10. Typically, a conventional compression fitting will be provided on the port 116 to allow connection via tubing. A second port 118 on the housing 114 provides for a power connector 120, which is connected to the wire coil heating element 110, and a plurality of temperature sensing leads 122, typically being thermocouple connectors. The leads 122 will be connected to thermocouple 124 located on a cage structure 130, attached to the distal end 106 of the elongate catheter body 102.

The cage structure 130 comprises four resilient elements or "ribs" 132 which are secured at a proximal end of the distal end of the catheter body 102 and to each other by means of a distal button 134. The individual elements 132 will be formed of a resilient material, such as spring steel, shape memory alloy, heat memory alloy (e.g., Nitinol®), or the like. As will be described in more detail hereinafter, the cage structure 130 will be introduced to the hollow body organ in a collapsed configuration within a suitable cannula or sheath, and will thereafter expand to the open configuration, as illustrated in FIGS. 11, 13, and 14.

A flow distributing element 140 is connected via a short tube 142 to the distal end of lumen 112 through catheter body 102. The flow distributing element 140 includes a plurality of flow ports 144 which are oriented to distribute flow in a preselected pattern. As best seen in FIG. 14, three flow ports 144 may be provided in order to direct flow in three diverging directions within a single plane. Such a configuration is particularly useful for thermal treatment of the uterus, as described hereinafter, where the outermost ports are generally directed at the cornua regions of the uterus which might otherwise receive insufficient heating from the catheter 100. Divergent angles $\alpha$, and $\alpha_2$ will usually be from 30° to 75°, thus subtending a total angle in the range from 60° to 150°.

Figure 15:
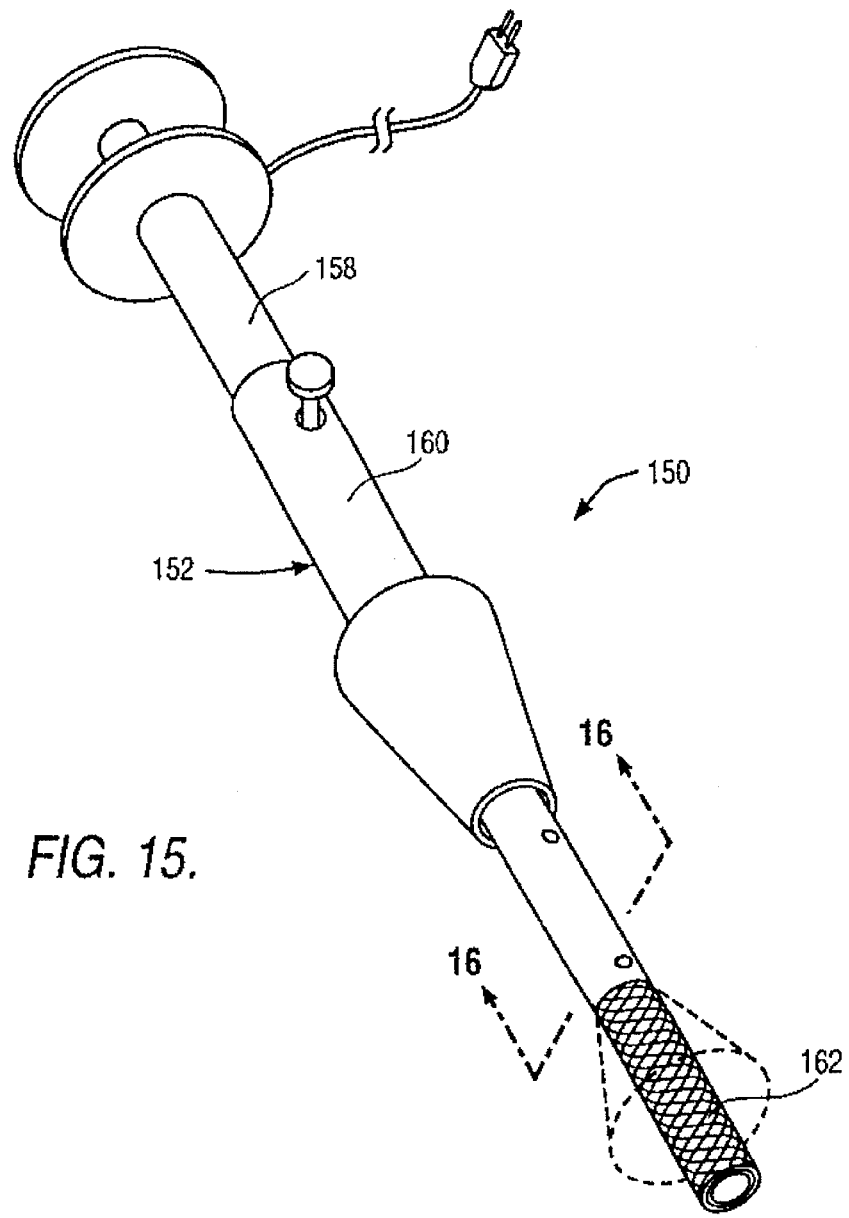
FIG. 15 is a perspective view illustrating a cannula useful for introducing the catheter of FIG. 11 to a uterus.
Figure 16:
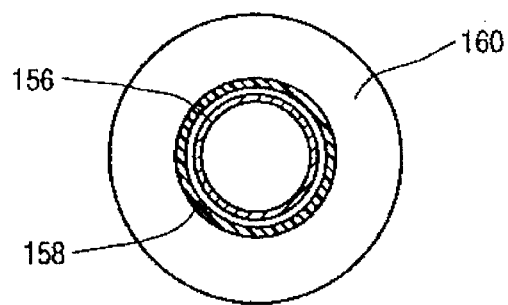
FIG. 16 is a cross-sectional view taken along line 16—16 of FIG. 15.
Figure 17:
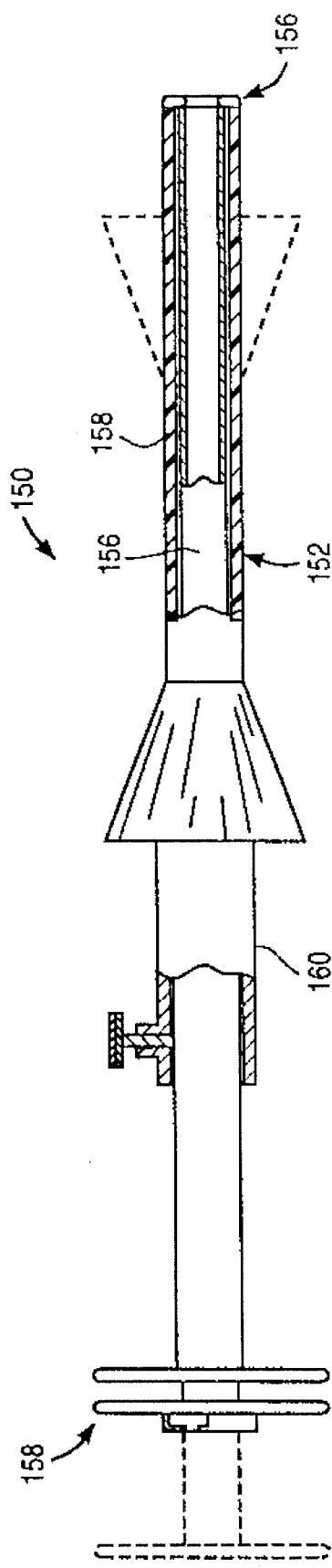
FIGS. 17 and 18 are side, elevational views of the catheter FIG. 11.
Figure 18:
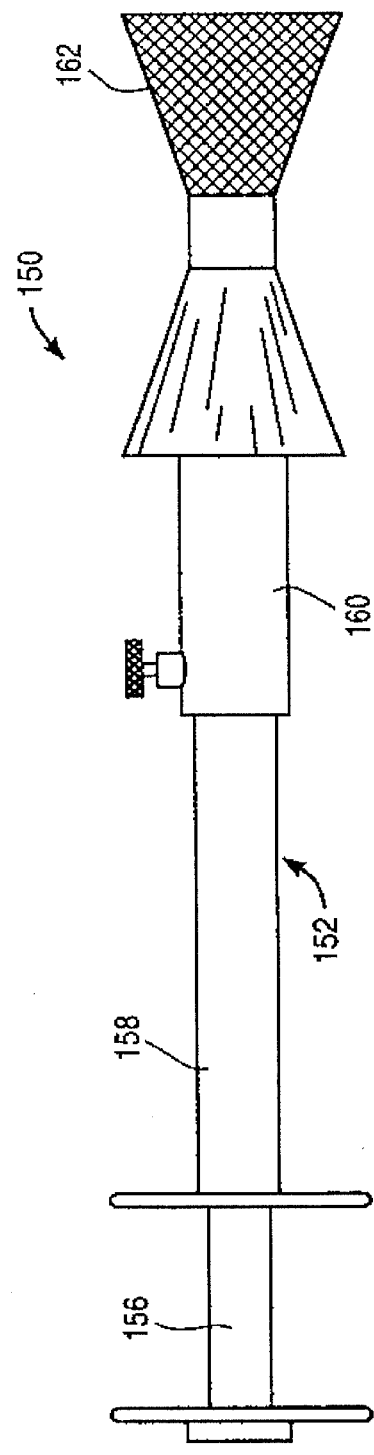

Referring now to FIGS. 15–18, an access cannula 150 suitable for use with the catheter 102 for thermal treatment of the uterus will be described. The access cannula 150 comprises an elongate body having a total length from about 20 cm to 40 cm and having an access lumen 154 extending from a distal end 156 to a proximal end 158 thereof. Construction and use of the uterine access cannula 150 is described in detail in co-pending application Ser. No. 03/266036, filed on the same date as the present application. Briefly, the cannula body 152 includes an inner tubular shaft 156, an outer tubular shaft 158, and an axially translatable outer cervical seal member 160, an expansible region 162, typically a cylindrical mesh, forms the distal region of the outer tubular shaft 158. When the inner tubular shaft 156 is fully inserted into the outer tubular shaft 158, as illustrated in FIGS. 15 and 17, the expansible region 162 will be collapsed. By pulling the inner tubular shaft 156 proximally relative to the outer tubular shaft 158, however, the expansible region 162 will be axially compressed so that its distal end expands radially to form a conical surface, as illustrated in broken line in FIGS. 15 and 17 and in full line in FIG. 18. As described in greater detail hereinafter, such expanded conical surface will form an inner cervical seal when the cannula 150 is introduced through the cervix into the uterus. The outer cervical seal member 60 may be axially translated relative to the inner cervical seal, so that the two seals may be brought together as illustrated in FIG. 18.

Figure 20:
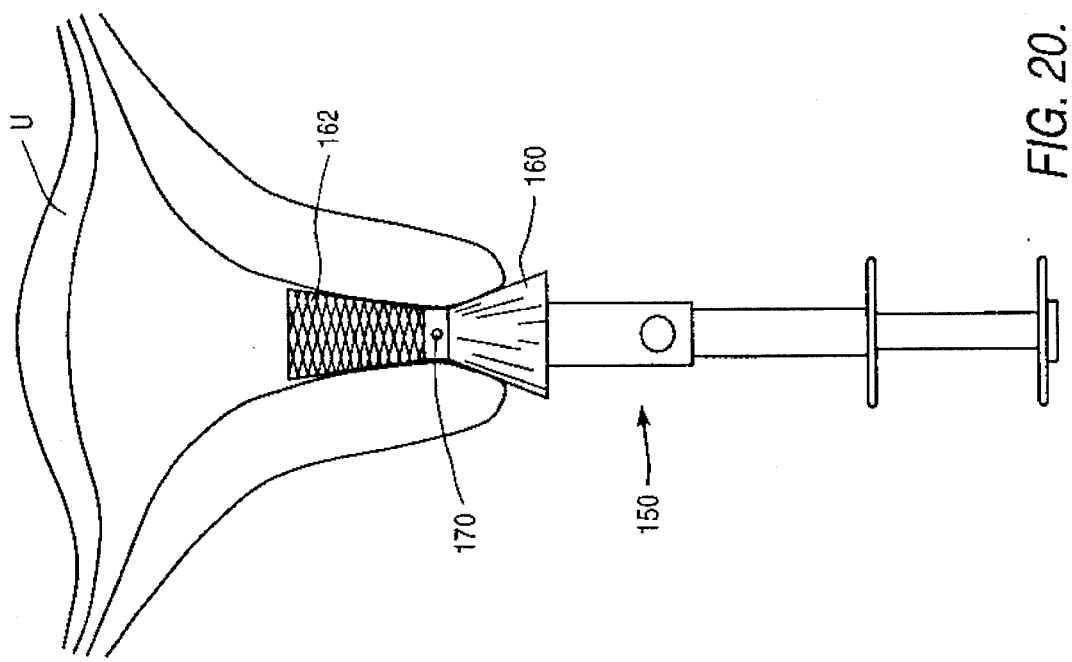
FIGS. 19–21 illustrate use of the catheter of FIG. 11 in thermally treating a uterus according to the present invention.
Figure 19:
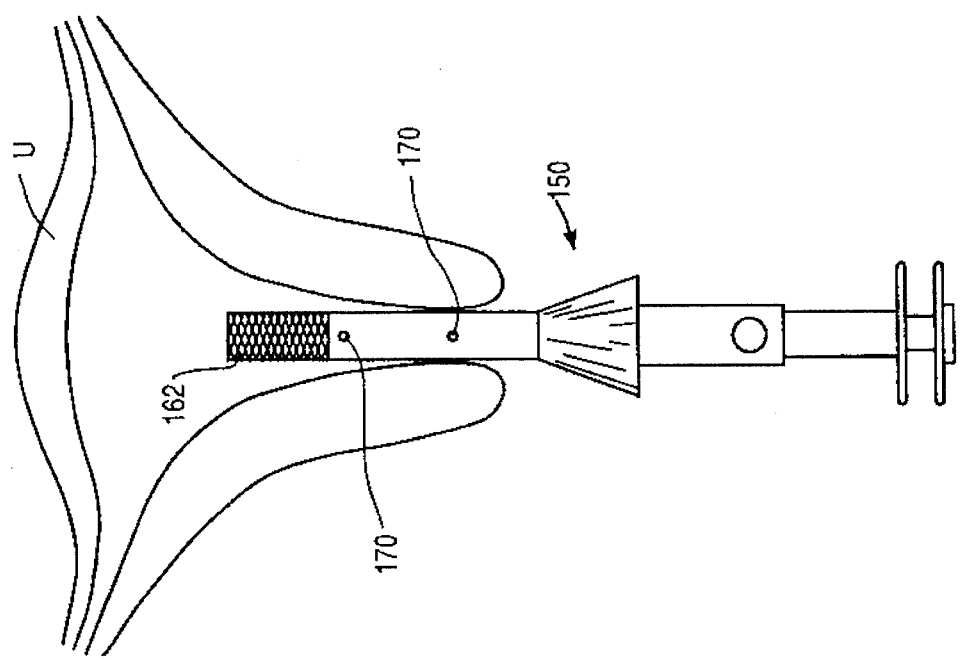
Figure 21:
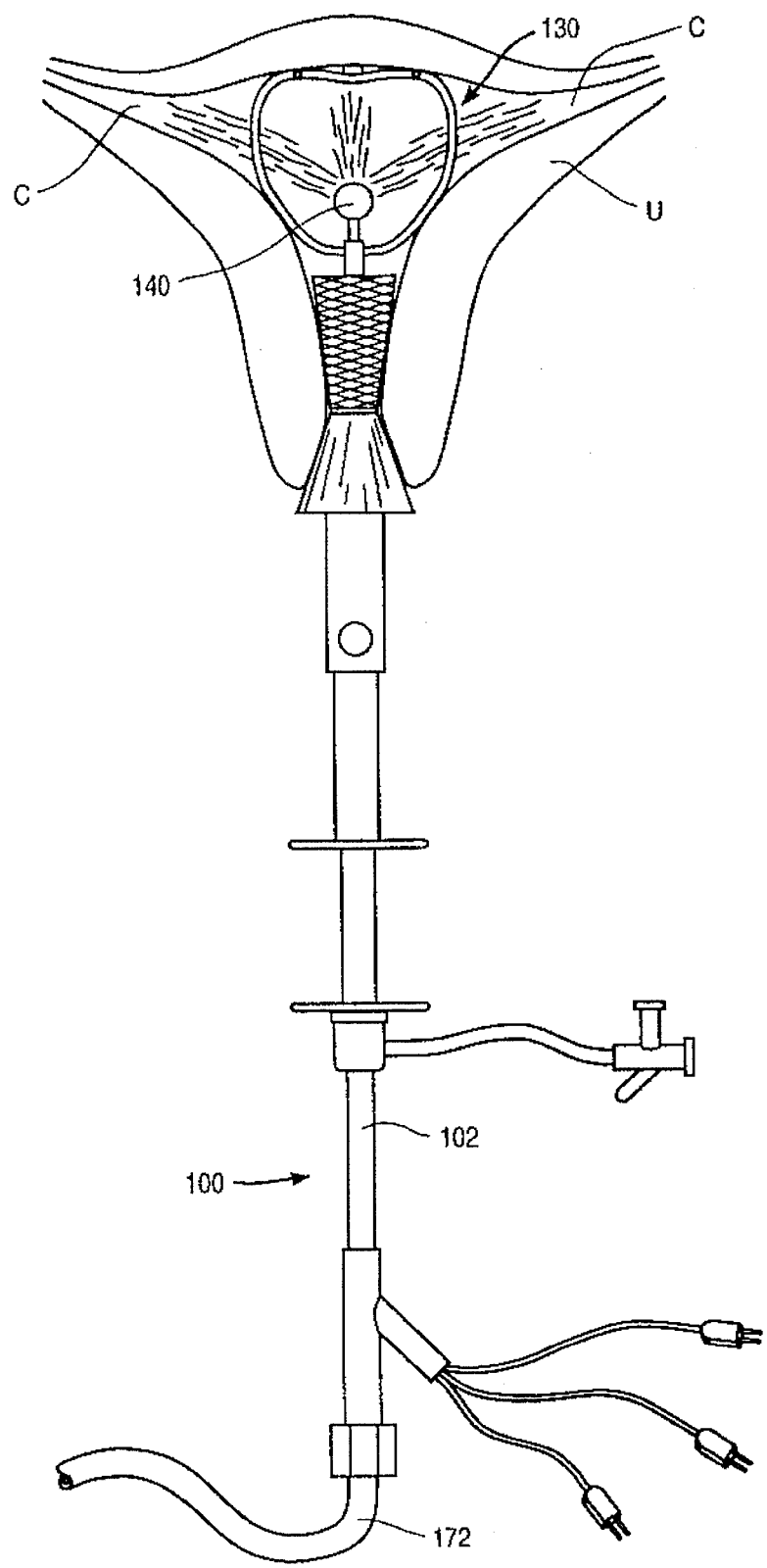

Referring now to FIGS. 19–21, use of the catheter 100 and uterine access cannula 150 in thermal treatment of a uterus U will be described. Access to the cervical os is obtained in a conventional manner. After access is obtained, the uterine access cannula 115 is introduced through the os while the inner cervical seal 116 is in its collapsed configuration, as illustrated in FIG. 19. The expansible region 162 is then expanded, as illustrated in FIG. 20, and drawn proximally outward so that it seals against the inner surface of the cervix. The outer cervical seal member 160 is then advanced distally so that the inner and outer surfaces of the cervix are engaged by the inner seal 162 and outer seal 160, respectfully. The cannula 150 thus provides a generally fluid tight seal about its periphery so that heated thermally conductive medium which is introduced as described hereinafter cannot leak around the cannula outwardly into the vagina.

After the uterine access cannula 150 is properly positioned, as illustrated in FIG. 19, catheter 100 is introduced through the central lumen of the cannula. The catheter 100 will be introduced so that cage structure 130 at its distal end expands into the interior of the uterus, maintaining an open volume for thermal treatment. The flow distributing element 140 will thus be located within the interior of the uterus so that fluid flow therefrom is directed toward the cornua regions C, in order to enhance thermal transfer to these regions. The center port 144 of the flow distributing element 140 will direct fluid centrally within the uterine cavity.

In order to assure that heated fluid is not leaking peripherally over the access cannula 150, temperature sensing elements 170 may be provided on its exterior surface over the regions where leakage might be expected. Means for monitoring the temperatures of these elements (not illustrated) is provided. Thus, if an unexpected temperature rise is detected, heated fluid can rapidly be withdrawn and treatment stopped until a better seal is achieved.

Heat treatment can be achieved by introducing a heated or unheated thermally conductive medium through the catheter 100 using connector tube 172. The connector tube will be connected to a suitable heating and oscillatory pumping system, such as illustrated in FIG. 10. The system will deliver electrical energy to the internal heating coils 110, while fluid is oscillated back and forth within the uterine cavity. Volumes and temperatures will generally be controlled as described above. The treatment will be continued for a time sufficient to induce necrosis of the endometrial lining of the uterus.

Figure 22:
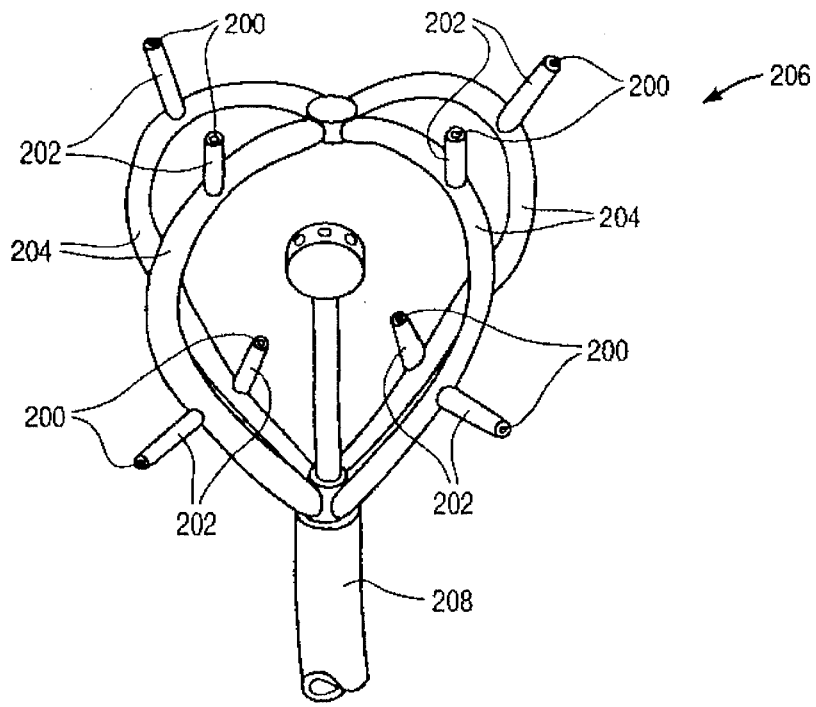
FIG. 22 illustrates an alternative cage structure for the catheter FIG. 11, further including temperature sensors mounted on penetrating elements on the cage structure.
Figure 23:
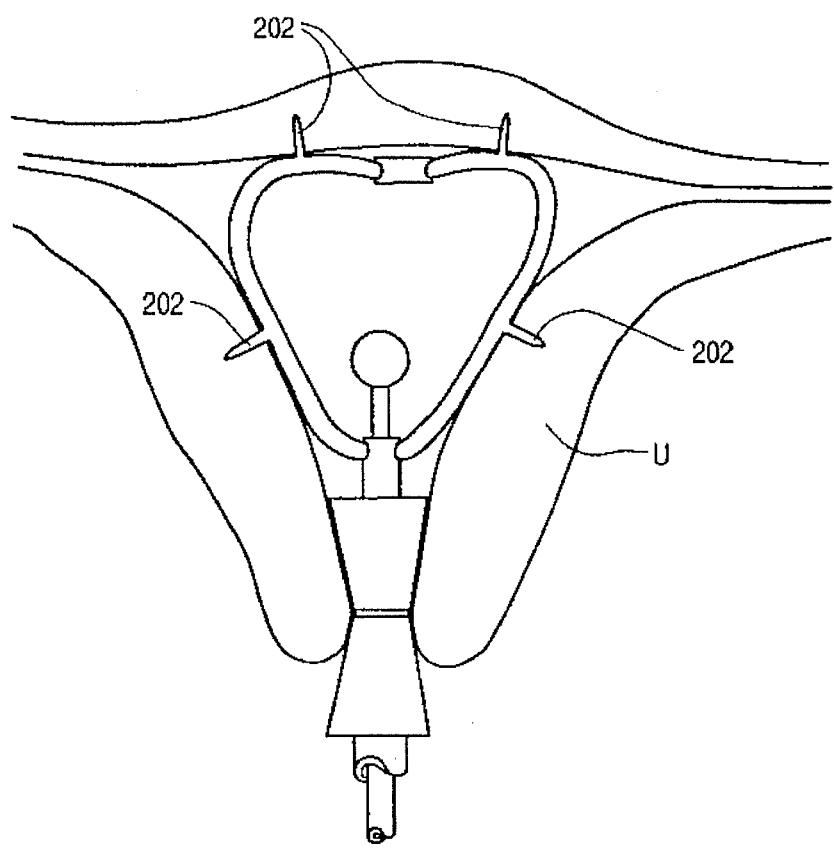
FIG. 23 illustrates disposition of the cage structure of FIG. 22 within a uterus, with the penetrating elements shown within the endometrial lining of the uterus.

A preferred temperature sensing system for the catheters of the present invention is illustrated in FIGS. 22 and 23. The temperature sensing system comprises a plurality of temperature sensing elements 200, typically thermocouples, which are located at the distal end of penetrating elements 202 which are disposed about individual resilient elements 204 of a cage structure 206 mounted at the distal end of a catheter body 208. The penetrating elements 202 are disposed generally radially outward from the cage structure so that they will penetrate by a predetermined depth into the uterine wall as illustrated in FIG. 23. The penetrating elements 202 will generally be resilient members which are collapsed while the catheter is introduced through a suitable cannula but which will spring back to the desired configuration when the catheter is released. The penetrating members 202 will thus be able to penetrate into the uterine wall as illustrated. The length of the penetrating members 202 will typically be in the range from 1 mm to 20 mm, preferably from 2 mm to 6 mm, corresponding to the desired penetration depth for measuring temperature.

Although the foregoing invention has been described in detail for purposes of clarity of understanding, it will be obvious that certain modifications may be practiced within the scope of the appended claims.

What is claimed is:

1. A fluid mixing and heating catheter, said catheter comprising:

an elongate member having a proximal end, a distal end, and a lumen extending therebetween;

a heating element disposed within at least a portion of the length of the lumen so that fluid flowing through the lumen will contact the heating element;

a fluid connector at the proximal end of the elongate member which connects the lumen to an external fluid source; and a power connector at the proximal end of the elongate member which connects the heating element to an external power source.

2. A fluid mixing and heating catheter as in claim 1, wherein the elongate member is a flexible tube having a length in the range from 10 cm to 100 cm and a lumen diameter in the range from 2 mm to 10 mm.

3. A fluid mixing and heating catheter as in claim 2, wherein the heating element is disposed within at least the distal-most 1 cm of the lumen.

4. A fluid mixing and heating catheter as in claim 1, wherein the heating element is a wire coil.

5. A fluid mixing and heating catheter as in claim 1, further comprising a layer of thermal insulation over at least a portion of an outside surface of the elongate member.

6. A fluid mixing and heating catheter as in claim 1, further comprising a fixture at the proximal end of the elongate member, which fixture comprises the fluid connector and power connector.

7. A fluid mixing and heating catheter as in claim 1, further comprising a flow directing element at the distal end of the lumen in the elongate member.

8. A fluid mixing and heating catheter as in claim 7, wherein the flow directing element has at least two ports for directing fluid flow in at least two different directions.

9. A fluid mixing and heating catheter as in claim 8, wherein at least two ports are directed to create a flow which diverges at an angle of about 60° to 150°.

10. A fluid mixing and heating catheter as in claim 1, further comprising a cage structure at the distal end of elongate member.

11. A fluid mixing and heating catheter as in claim 10, wherein the cage structure is expansible from a collapsed configuration to an expanded configuration which defines a heating volume therein.

12. A fluid mixing and heating catheter as in claim 11, wherein the cage structure is resilient so that it assumes the collapsed configuration when constrained and reassumes the expanded configuration when released from being constrained.

13. A fluid mixing and heating catheter as in claim 10, further comprising at least one temperature sensing element on the cage structure.

14. A fluid mixing and heating catheter as in claim 13, wherein the temperature sensing element comprises a penetrating member having a temperature transducer at a distal end thereof, where the penetrating member is disposed on the expansible cage, so that it will penetrate tissue adjacent to the cage when said cage is expanded.

15. A fluid mixing and heating catheter as in claim 14, wherein the penetrating member has a length of at least about 1 mm.

16. A system for mixing and heating a thermally conductive fluid within a hollow body organ, said system comprising:

a fluid mixing and heating catheter as in claim 1;

a power supply which connects to the power connector or the catheter; and an oscillatory pump which connects to the fluid connector on the catheter.

17. A system as in claim 16, wherein the elongate member is a flexible tube having a length in the range from 10 cm to 100 cm and a lumen diameter in the range from 2 mm to 10 mm.

18. A system as in claim 17, wherein the heating element is disposed within at least the distal-most 1 cm of the lumen.

19. A system as in claim 16, wherein the heating element is a wire coil.

20. A system as in claim 16, further comprising a layer of thermal insulation over at least a portion of an outside surface of the elongate member.

21. A system as in claim 16, further comprising a fixture at the proximal end of the elongate member, which fixture comprises the fluid connector and power connector.

22. A system as in claim 16, further comprising a flow directing element at the distal end of the lumen in the elongate member.

23. A system as in claim 22, wherein the flow directing element has at least two ports for directing fluid flow in at least two different directions.

24. A system as in claim 23, wherein at least two ports are directed to create a flow which diverges at an angle of about 30° to 180°.

25. A system as in claim 16, further comprising a cage structure at the distal end of elongate member.

26. A system as in claim 25, wherein the cage structure is expansible from a collapsed configuration to an expanded configuration which defines a heating volume therein.

27. A system as in claim 26, wherein the cage structure is resilient so that it assumes the collapsed configuration when constrained and reassumes the expanded configuration when released from being constrained.

28. A system as in claim 25, further comprising at least one temperature sensing element on the cage structure and a temperature controller which modulates power delivery from the power supply to the catheter.

29. A system as in claims 28, wherein the temperature sensing element comprises a penetrating member having a temperature transducer at a distal end thereof, wherein the penetrating member has a length of at least 1 mm and is disposed on the expansible cage, so that it will penetrate tissue adjacent to the cage when said cage is expanded.

30. A system as in claim 29, wherein the oscillatory pump is connected to an open fluid reservoir.

31. A fluid mixing and heating catheter comprising;

an elongate member having a proximal end, a distal end, and a lumen extending therebetween;

a heating element disposed within the lumen so that fluid flowing through the lumen will contact the heating element; and a flow directing element at the distal end of the lumen in the elongate member.

32. A fluid mixing and heating catheter as in claim 31, wherein the elongate member is a flexible tube having a length in the range from 10 cm to 100 cm and a lumen diameter in the range from 2 mm to 10 mm.

33. A fluid mixing and heating catheter as in claim 31, wherein the heating element is distributed over at least the distal-most 1 cm of the lumen.

34. A fluid mixing and heating catheter as in claim 33, wherein the heating element is a wire coil.

35. A fluid mixing and heating catheter as in claim 31, further comprising a layer of thermal insulation over at least a portion of an outside surface of the elongate member.

36. A fluid mixing and heating catheter as in claim 31, further comprising a fixture at the proximal end of the elongate member, which fixture comprises a fluid connector, a power connector, and a temperature sensor connector.

37. A fluid mixing and heating catheter as in claim 31, wherein the flow directing element has at least two ports for directing fluid flow in at least two different directions.

38. A fluid mixing and heating catheter as in claim 37, wherein at least two ports are directed to create a flow which diverges at an angle of about 60° to 150°.

39. A fluid mixing and heating catheter as in claim 31, further comprising a cage structure at the distal end of elongate member disposed over the flow directory element.

40. A fluid mixing and heating catheter as in claim 39, wherein the cage structure is expansible from a collapsed configuration to an expanded configuration which defines a heating volume therein.

41. A fluid mixing and heating catheter as in claim 40, wherein the cage structure is resilient so that it assumes the collapsed configuration when constrained and reassumes the expanded configuration when released from being constrained.

42. A fluid mixing and heating catheter as in claim 39, further comprising at least one temperature sensing element on the cage structure.

43. A fluid mixing and heating catheter as in claims 42, wherein the temperature sensing element comprises a penetrating member having a temperature transducer at a distal end thereof, where the penetrating member is disposed on the expansible cage, so that it will penetrate tissue adjacent to the cage when said cage is expanded.

44. A fluid mixing and heating catheter as in claim 43, wherein the penetrating member has a length of at least about 1 mm.

45. A system for mixing and heating a thermally conductive fluid within a hollow body organ, said system comprising;

a fluid mixing and heating catheter as in claim 16;

a power supply which connects to the heating element on the catheter; and an oscillatory pump which connects to the lumen in the elongate member.

46. A system as in claim 45, wherein the elongate member is a flexible tube having a length in the range from 10 cm to 100 cm and a lumen diameter in the range from 2 mm to 10 mm.

47. A system as in claim 45, wherein the heating element is disposed within at least the distal-most 1 cm of the lumen.

48. A system as in claim 47, wherein the heating element is a wire coil.

49. A system as in claim 46, further comprising a layer of thermal insulation over at least a portion of an outside surface of the elongate member.

50. A fluid mixing and heating catheter as in claim 45, further comprising a fixture at the proximal end of the elongate member, which fixture comprises the fluid connector and a power connector.

51. A system as in claim 45, wherein the flow directing element has at least two ports for directing fluid flow in at least two different directions.

52. A system as in claim 51, wherein at least two ports are directed to create a flow which diverges at an angle of about 60° to 150°.

53. A system as in claim 45, further comprising a cage structure at the distal end of elongate member dispose over the flow directing element.

54. A system as in claim 53, wherein the cage structure, is expansible from a collapsed configuration to an expanded configuration which defines a heating volume therein.

55. A system as in claim 54, wherein the cage structure is resilient so that it assumes the collapsed configuration when constrained and reassumes the expanded configuration when released from being constrained.

56. A system as in claim 53, further comprising at least one temperature sensing element on the cage structure.

57. A system as in claim 56, wherein the temperature sensing element comprises a penetrating member having a temperature transducer at a distal end thereof, where the penetrating member is disposed on the expansible cage, so that it will penetrate tissue adjacent to the cage when said cage is expanded.

58. A system as in claim 57, wherein the penetrating member has a length of at least about 1 mm.

59. An improved fluid mixing and heating catheter of the type including an elongate body having a proximal end, a distal end, and a lumen therebetween, and a heating element, wherein the improvement comprises locating the heating element within the lumen so that fluid will contact the heating element when passing through the lumen.

60. An improved mixing and heating catheter as in claim 59, wherein the elongate body is a flexible tube having a length in the range from 10 cm to 100 cm and a lumen diameter in the range from 2 mm to 10 mm.

61. An improved fluid mixing and heating catheter as in claim 60, wherein the heating element is disposed within at least the distal-most 1 cm of the lumen.

62. An improved fluid mixing and heating catheter as in claim 61, wherein the heating element is a wire coil.

63. A fluid mixing and heating catheter as in claim 60, further comprising a layer of thermal insulation over at least a portion of an outside surface of the elongate body.

64. An improved fluid mixing and heating catheter as in claim 59, wherein the improvement further comprises a flow directing element at the distal end of the lumen in the elongate member.

65. An improved fluid mixing and heating catheter as in claim 64, wherein the improvement further comprises a cage structure at the distal end of elongate member formed over the flow directing element.

66. An improved fluid heating and mixing catheter of the type including an elongate body having a proximal end, a distal end, and a lumen therebetween, and a heating element, wherein the improvement comprises a flow directing element at the distal end of the lumen and a cage structure surrounding the flow directing element.

67. An improved fluid mixing and heating catheter as in claim 59, wherein the elongate body is a flexible tube having a length in the range from 10 cm to 100 cm and a lumen diameter in the range from 2 mm to 10 mm.

68. A improved fluid mixing and heating catheter as in claim 67, wherein a heating element disposed the improvement further comprises within at least the distal-most 1 cm of the lumen.

69. An improved fluid mixing and heating catheter as in claim 66, wherein the flow directing element has at least two ports for directing fluid flow in at least two different directions.

70. An improved fluid mixing and heating catheter as in claim 69, wherein at least two ports are directed to create a flow which diverges at an angle of about 60° to 150°.

71. An improved fluid mixing and heating catheter as in claim 70, wherein the improvement further comprises a cage structure at the distal end of elongate member disposed over the flow directing element.

72. An improved fluid heating and mixing catheter of the type including an elongate body having a proximal end, a distal end, and a lumen therebetween, a heating element, and a cage structure disposed over the distal end of the elongate body, wherein the improvement comprises at least one temperature sensor disposed on the cage structure to contact an inner surface of a hollow body organ when the cage is located therein.

73. An improved fluid mixing and heating catheter as in claim 72, wherein the elongate body is a flexible tube having a length in the range from 10 cm to 100 cm and a lumen diameter in the range from 2 mm to 10 mm.

74. A fluid mixing and heating catheter as in claim 73, wherein the improvement further comprises a heating element disposed within at least the distal-most 1 cm of the lumen.

75. A fluid mixing and heating catheter as in claim 72, wherein the improvement further comprises a flow directing element at the distal end of the lumen in the elongate member.

76. An improved fluid mixing and heating catheter as in claim 72, wherein the cage structure is expansible from a collapsed configuration to an expanded configuration which defines a heating volume therein.

77. An improved fluid mixing and heating catheter as in claim 76, wherein the cage structure is resilient so that it assumes the collapsed configuration when constrained and reassumes the expanded configuration when released from being constrained.

78. An improved fluid mixing and heating catheter as in claim 72, wherein the temperature sensing element comprises a penetrating member having a temperature transducer at a distal end thereof, where the penetrating member is disposed on the expandable cage, so that it will penetrate tissue adjacent the cage when said cage is expanded.

79. An improved fluid mixing and heating catheter as in claim 78, wherein the penetrating member has a length of at least about 1 mm.

\* \* \* \* \*